US008612246B2

(12) United States Patent
Eggena et al.

(10) Patent No.: US 8,612,246 B2
(45) Date of Patent: Dec. 17, 2013

(54) CLINICAL GUIDELINES ENGINE

(75) Inventors: Timothy Eggena, Hamilton, GA (US);
Bryan Rosenberger, Pennsburg, PA (US); Robert Hale, Atlanta, GA (US); Robert Nary, Voorhees, NJ (US); Robert Ellis, Doylestown, PA (US); Patrick Cline, Southlake, TX (US)

(73) Assignee: QSI Management, LLC, Irvine, CA (US)

( * ) Notice: Subject to any disclaimer, the term of this patent is extended or adjusted under 35 U.S.C. 154(b) by 591 days.

(21) Appl. No.: 12/377,301

(22) PCT Filed: Jan. 3, 2008

(86) PCT No.: PCT/US2008/000107
§ 371 (c)(1),
(2), (4) Date: Apr. 13, 2009

(87) PCT Pub. No.: WO2008/085881
PCT Pub. Date: Jul. 17, 2008

(65) Prior Publication Data
US 2010/0211402 A1    Aug. 19, 2010

Related U.S. Application Data

(60) Provisional application No. 60/883,189, filed on Jan. 3, 2007.

(51) Int. Cl.
*G06Q 10/00* (2012.01)
*G06Q 50/00* (2012.01)

(52) U.S. Cl.
USPC .................... 705/2; 705/3; 600/300

(58) Field of Classification Search
USPC .......................... 705/2–3; 600/300
See application file for complete search history.

(56) References Cited

U.S. PATENT DOCUMENTS

| 2003/0212580 | A1 | 11/2003 | Shen |
| 2004/0261063 | A1 * | 12/2004 | Wang et al. .................. 717/136 |
| 2005/0108046 | A1 * | 5/2005 | Craft ................................ 705/2 |
| 2005/0148829 | A1 | 7/2005 | Abraham-Fuchs et al. |

FOREIGN PATENT DOCUMENTS

| WO | 2005003892 | 1/2005 |
| WO | 2006035383 | 4/2006 |

* cited by examiner

*Primary Examiner* — Luke Gilligan
(74) *Attorney, Agent, or Firm* — Fish & Associates, PC

(57) ABSTRACT

A medical guideline integration engine is presented. The engine imports medical guideline information from disparate sources based on various guideline standards into a knowledge base. The knowledge base houses the information in a database. Upon request, the engine retrieves the information from the knowledge base and converts the information into a desired guideline format.

6 Claims, 1 Drawing Sheet

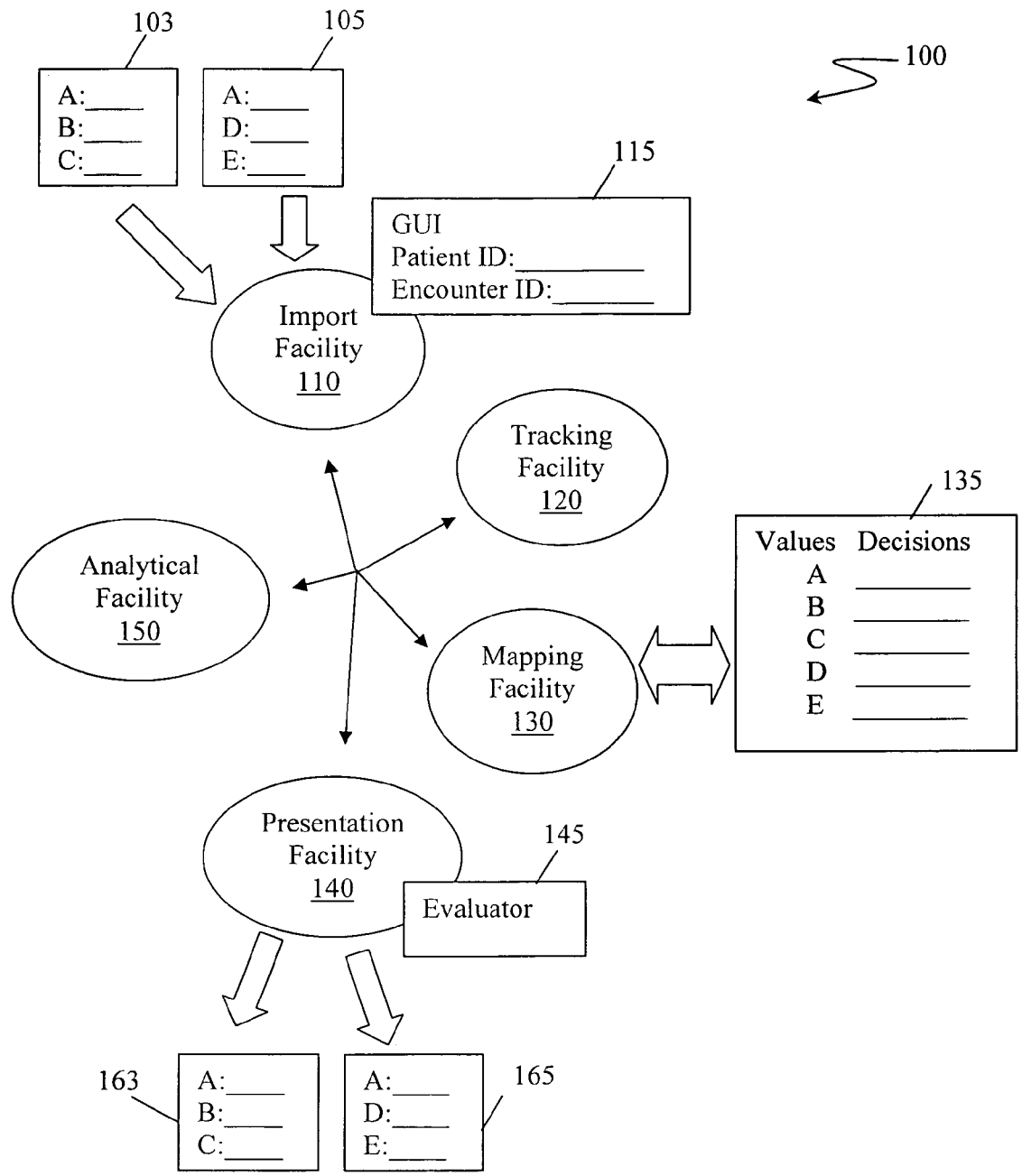

CLINICAL GUIDELINES ENGINE

This application claims benefit to U.S. Provisional Application No. 60/883,189 filed on Jan. 3, 2007. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is data processing systems for patient care.

BACKGROUND OF THE INVENTION

Medical providers have become quite adept at using information technology (IT) for scheduling, order entry, costs capturing, clinical records, billing, and financial reporting. Some providers have also harnessed IT to implement various patient safety programs and clinical decision support. See for example the Brigham integrated computing system (BICS) implemented at Brigham and Women's Hospital in Boston Mass.

A huge problem remains, however, in that different clinical decision support systems are generally incompatible with each other. One approach has been to develop standardized formats for sharing and implementing point-of-care guidelines. These include: GuideLine Interchange Format (GLIF); Guideline Elements Model (GEM); Digital electronic Guidelines Library (DeGeL); and Asbru Guidelines Ontology.

Some computer systems have been implemented to integrate different guideline standards. WO 2005/003892 to Wang teaches a computer system that translates the different standardized formats into a generic translated guideline, and executes the translated guideline. Wang, however, simply creates a new generic guideline that takes existing guidelines as input, instead of truly creating an integrated software. Additionally, executing a generic translated guideline eliminates many of the advantages of the original standardized format.

WO 2006/035383 to Alsafadi teaches a database system that displays the different standardized formats. The different standardized formats can be displayed specifically, generally, or at intermediate levels of abstraction. Alsafadi, however, does not help to translate the different standardized formats into one more familiar to the institution. While customized views of a format may be created, the customized view must be created manually by the individual user by bypassing steps in the guideline instead of actually translating the view from one format into another.

Problems remain, however, in that these different formats are themselves incompatible, and it appears that the various institutions that develop and endorse particular systems and formats are loathe to relinquish their own work in favor of other standards. Thus, there is still a need in the medical care industry for integrating divergent guidelines standards.

SUMMARY OF THE INVENTION

The present invention provides systems and methods in which a medical guidelines integration engine imports multiple guidelines, maps the guidelines into a common set of standards, and presents guidelines from the common set of standards to a plurality of other sets of standards. The integration engine preferably has separate facilities to perform different tasks, for example an import facility, a mapping facility, and a presentation facility. As used herein, the term "facility" broadly includes relevant physical apparatus, interfaces, communication means, and computer software, regardless of implementation. Thus, for example, the term "facility" includes relevant software, regardless of whether the software is client or server based, and regardless of whether the software is divided into modules, stand-alone programs, and so forth.

In preferred embodiments the import facility preferably includes a Graphical User Interface (GUI) that captures a patient identifier and an encounter identifier, signs/symptoms, laboratory information, and other relevant information. Also in preferred embodiments, the mapping facility maps values and decision variables of each of the guidelines. The presentation facility preferably comprises an evaluator that accepts a call to initiate itself, and then it passes results back to a calling application. The engine can also advantageously include a compliance tracking facility that receives data relative to whether a practitioner or other healthcare provider followed the first guideline, and an analytical facility that compares an outcome of a group of patients that deviated from the first guideline, as opposed to another group of patients where there was no deviation.

BRIEF DESCRIPTION OF THE DRAWING

FIG. 1 is a schematic of an embodiment of a clinical guideline engine.

DETAILED DESCRIPTION

A. Overview

In FIG. 1 a Clinical Guidelines Engine 100 (CGE) incorporates one or more of input guidelines 103 and 105, preferably from a multiplicity of sources including for example, third party content vendors, clinical staff and end users. CGE 100 receives patient-specific data, and provides medical care guidance with respect to that data.

Preferred CGE 100 has support for a large number of decision variables represented by the alphanumeric labels within guidelines 103 and 105, and integrates variables and logic from disparate guidelines systems such that clients are able to cross reference their template fields to the decision variables in CGE 100. Thus, knowledge base 135 can be implemented with decision variables or logic already configured. Additionally, CGE 100 can utilized template triggers in an electronic medical records system (EMR; not shown) which, for example, can enable the decision variables to be evaluated by CGE 100. Once evaluated, CGE 100 generally provides results as a set of recommendations represented by one or more of output guidelines 163 and 165.

CGE 100 can be implemented using any suitable data interchange format(s), including for example XML. Preferred embodiments of CGE 100 advantageously support the GEM and Asbru ontologies. As new and updated guidelines in these ontologies are made available, they can be mapped to CGE 100 systems. Clients also preferably have the ability to map new guidelines to the CGE through a graphical user interface. For example, a user interface can enable an end user to create or define the guideline to the system, thereby, making it available CGE 100. Once the guideline has been described to CGE 100, its content can be mapped to knowledge base 135.

It is contemplated that CGE 100 can distinguish between guideline 103 and guideline 105 developed and endorsed by various institutions and/or groups by parsing data structures or content within the guidelines. For example, guideline 103 could be created in with GLIF, and guideline 105 could be created by GEM. Additionally, it is contemplated that an administrator of CGE 100 is able to group guidelines into custom guideline sets. Medical practices can then determine which guideline sets they wish to implement with in their practices given availability of resources.

B. Technical Description

The following technical description refers one preferred embodiment currently contemplated to be implement by NextGen™ of NextGen Healthcare Information Systems, Inc. of Horsham, Pa.

A preferred embodiment of CGE 100 comprises several facilities among others: guidelines import facility 110, mapping facility 130, and presentation facility 140.

A preferred guidelines import facility 110 has a guideline import module (GIM) that imports one or more of input guidelines 103 and 105 into CGE 100. Guidelines 103 and 105 can represent substantially different guideline standards which can be automatically identified by CGE 100 through parsing, header information, metadata, or other known methods. Generally, guideline 103 and guideline 105 are at least partially incompatible. Although guidelines are preferably in XML format, other suitable guideline formats are contemplated including CSV, or HTML. As guideline content is created and modified, the GIM accepts the updated content and prepare it for operation in CGE 100.

In some embodiments guidelines import facility 110 also includes a guidelines description module (GDM), possibly through GUI 115, which enables staff and end users to create or define a new guideline definition to CGE 100. Preferably, guidelines are properly defined for use by CGE 100 before a specific guideline is imported from a source.

Preferred guidelines mapping facility 130 includes a guideline mapping module (GMM; not shown) that provides a mechanism for staff and end users to map the decision variables in the guideline to values in knowledge base 135. Knowledge base 135 is an aggregated common set of standard guidelines that can be accessed by individuals regardless of a required format. Once the data is collected, the guidelines can be presented to the individual in the required format. Both decision elements, decision logic, and individual values are mapped to the database fields. Knowledge base 135 can be implemented using any suitable database system including, for example, a SQL, an Oracle™ database or other commercial data storage system. Due to the differences in guideline formats, one should appreciated that the mappings of decision elements, logic, or values do not necessarily have a one-to-one correspondence from one guideline standard to another. Therefore, knowledge base 135 preferably support many-to-many or otherwise supports multiply linking fields.

CGE 100 maps decision variables to discrete data fields in the EMR as represented by knowledge base 135. When the user invokes the guidelines engine through a template trigger, CGE 100 evaluates the decision variables and determines the guidelines appropriate for the current patient. CGE 100 accepts a patient identifier and an encounter identifier, preferably through GUI 115. This will determine the data that it used later in guideline analysis.

CGE 100 also includes tracking facility 120 with a Guidelines Compliance Evaluator (GCE) module (not shown). For example, at the point of care, a health care provide can input their patient care information (e.g. treatments, outcomes, diagnosis, etc. . . . ) into CGE 100. The GCE reviews data reported to CGE 100 by tracking compliance of the guidelines. Tracking facility 120 receives data relative to whether a practitioner or other healthcare provider follows one or more of guidelines 103 or 105. Tracking facility 120 preferably provides a graphical display or analysis capabilities which enables an administrator to determine the level of compliance by the end users. Such compliancy tracking provides for several benefits. CGE 100 can be used to track compliancy of best practices, can be used for research purposes, or can be used to indicating when healthcare providers require training.

For example, a preferred CGE 100 provides analysis of data within knowledge base 135 through analytical facility 150. Information concerning the outcome of patient treatment can be collected from knowledge base 135. It is contemplated that patients can be categorized into at least two groups: those whose treatment deviated from the guidelines and those whose treatment did not deviate from the guidelines. The outcome of the treatments can then be compared and contrasted to research if a best practice can be improved. The results of the analysis can then be presented to a user of CGE 100.

CGE 100 also includes presentation facility 140. Presentation facility 140 translates guidelines information from knowledge base 135 into one or more of output guidelines 163 and 165. Output guidelines 163 and 165 could be in the same format or structure as input guidelines 103 and 105 or could be any other suitable guideline format. For example, when input guidelines 103 and 105 are imported using GEM format, guideline 163 could be presented as GLIF recommendation or guideline 165 could be presented as a DeGeL recommendation. An institution with a system that is designed to implement guidelines in a GLIF recommendation can set presentation facility 140 to present all guidelines in a GLIF format by default. In some embodiments, the presentation facility renders output guidelines 163 and 165 in a structured data format including XML, HTML, or other computer readable formatting structures.

It is also contemplated that presentation facility 140 includes guideline evaluator (GE) 145. GE 145 analyzes patient information and presents recommendations. Upon a request from a user of CGE 100, GE 145 queries knowledge base 135 for patient information. GE 145 then compiles the result set into a desired form for the requesting application. In preferred embodiments, GE 145 accepts a WEB Service, or other network request (e.g. TCP, UDP, HTTP, HTML, SQL, etc. . . . ), to launch or otherwise initialize itself. GE 145 passes results from the request back to a calling application for presentation to a user.

C. Example Architecture

In the contemplated NextGen™ implementation, each of the different components is architected based upon its operation. Since import facility 110 brings new and updated guidelines content in from disparate sources, the import facility is preferably implemented as a WEB service. One should note that performance is not critical for the operation of CGE 100, however, it is contemplated that the system responds with low latency, preferably in less than 10 seconds, and more preferably less than 1 second.

Import facility 110 and mapping facility 130 preferably have a rich user interface that provides users the ability to import guideline formats (e.g. standardized or proprietary formats). These modules are preferably developed using C#, Java, or other high-level programming languages having smart component or browser technology integration. GE 145 is contemplated to be a work horse or black box that does not require a user interface and can be developed using any suitable service oriented technology.

D. Example Requirements of an Especially Preferred Embodiment

One should note the following requirements for the various modules are presented for clarity. One skilled in the art should appreciated that alternative requirements are possible while remaining within the scope of the inventive subject matter.

In this case the Guidelines Import Module (GIM) of Import Facility 110 accepts defined XML data streams representing defined guidelines; preferably accepts guidelines formatted in GEM or Asbru; reads the guideline descriptions created by the GDM and process and store incoming guideline data; creates new decision variable definitions; imports an existing XML guideline description; provides support for additional ontologies; and associates the guideline with the institution that created it and the institution(s) that endorses it.

The Guidelines Description Module (GDM) has the following functions: Enables end users to describe guideline to CGE 100; provides a tag for the GIM to tie the GDM guideline description with new guideline information being accepted by the GIM; provides a method to indicate the institution that created the guideline; provides a method to indicate the institution(s) that endorse the guideline; provides a method for a guideline administrator to create custom guideline sets; and includes an easy to use graphical XML editor that provides users the ability to select a supported XML schema and populate it with their guideline documentation.

E. The Guidelines Mapping Module (GMM) of Mapping Facility 130 Ties the Decision Variables in CGE 100 to the Discrete Data Fields in Knowledge Base 135.

Incorporates new fields as new template fields are added; the new fields dynamically appear in the list in order to be mapped.

Groups CGE 100 decision variables to ease locating a fields.

Groups knowledge base 135 database fields to ease locating database fields.

Provides a default table display for knowledge back 135 fields.

Provides an interface that allows an application to provide a database field table that identifies the tables and columns available for mapping; thereby, making the module transportable from the database system to others.

Provided available fields to the GMM when the product and the knowledge base updates are made to the database field tables.

Changes all existing references in all mapped guidelines based on changed in the database field table. For instance, if the a group replaces a field in the knowledge base that had a number of decision variables associated with it across a group of guidelines there will be an operation that will allow the substitution of the new data field for the old one.

Guideline Evaluator (GE) of Evaluator 145 supports at least some of the following operations: start a session; record a decision variable; provide a list of necessary decision variables; evaluate the collected decision variables; deliver recommended guideline results; evaluate all enabled guidelines to determine which guidelines are appropriate to present to the end user; preferably step through a guideline and evaluate the decision variables to determine what guidelines should be presented; determines which guideline sets will be used for a given practice and/or user; and preferably accepts information that indicates whether the user followed the guideline. This could be accomplished by way of communication with the application of through predefined database structure.

The Guideline Compliance Evaluator (GCE) of Tracking Facility 120 shows compliance by doctor (e.g. diagnosis, guideline set, etc. . . . ); and shows a history of deviations from a given guideline.

It should be apparent to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps could be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A medical guidelines integration engine comprising:
   a guideline import facility comprising a first processor that executes software instructions stored on a first non-transitory memory, and configured to import both (a) a first guideline that uses a first set of standards, and (b) a second guideline that uses a second set of standards that is at least partially incompatible with the first set of standards including with respect to decision variables;
   a mapping facility comprising a second processor that executes software instructions stored on a second non-transitory memory, and configured to map each of the first and second guidelines into a common set of standards where the incompatible decision variables are mapped into integrated decision variables; and
   a presentation facility comprising a third processor that executes software instructions stored on a third non-transitory memory, and configured to map from the common set of standards, including the integrated decision variables, to an automatically recommended guideline standard from a plurality of other sets of guideline standards, and to present an automatically recommended guideline according to the recommended guideline standard.

2. The engine of claim 1, wherein the import facility includes a Graphical User Interface (GUI) configured to capture a patient identifier and an encounter identifier.

3. The engine of claim 1, wherein the mapping facility is further configured to map values and decision variables of each of the guidelines into the integrated decision variables.

4. The engine of claim 1, wherein the presentation facility comprises an evaluator configured to accept a call to initiate itself, and configured to pass results back to a calling application.

5. The engine of claim 1, further comprising a compliance tracking facility configured to receive data relative to whether a practitioner followed the first guideline.

6. The engine of claim 1, further comprising an analytical facility configured to compare an outcome of a group of patients that deviated from the first guideline, as opposed to another group of patients where there was no deviation.

\* \* \* \* \*